United States Patent [19] [11] Patent Number: 5,872,143
Tanaka et al. [45] Date of Patent: Feb. 16, 1999

[54] INSECTICIDAL AEROSOL COMPOSITION AND INSECTICIDAL COMPOSITION FOR PREPARATION OF SAME

[75] Inventors: Yasuyori Tanaka, Toyonaka; Tadahiro Matsunaga, Kobe, both of Japan

[73] Assignee: Sumitomo Chemical Company, Limited, Osaka, Japan

[21] Appl. No.: 907,089

[22] Filed: Aug. 6, 1997

[30] Foreign Application Priority Data

Aug. 7, 1996 [JP] Japan ..................................... 8-208464

[51] Int. Cl.$^6$ ................................................. A61K 31/415
[52] U.S. Cl. ............................................................ 514/389
[58] Field of Search ............................................. 514/389

[56] References Cited

U.S. PATENT DOCUMENTS 4,176,189  11/1979  Itaya et al. ........................... 424/273 R

FOREIGN PATENT DOCUMENTS 0 320 909 A1   6/1989   European Pat. Off. .
0 370 321 A1   5/1990   European Pat. Off. .
1 256 417     12/1971   United Kingdom .
2 243 297     10/1991   United Kingdom .

OTHER PUBLICATIONS

Chemical Abstracts vol. 114: 88409w (Terdos et al), 1991.
Chemical Abstracts vol. 103: 83550y (Fumakiua Ltd), 1985.

*Primary Examiner*—Leonard Schenkman
*Attorney, Agent, or Firm*—Pillsbury Madison & Sutro LLP

[57] ABSTRACT

A pre-mix insecticidal composition is disclosed that contains (a) 0.1–10% by weight of 2,4-dioxo-1-(2-propynyl) imidazolidin-3-ylmethyl chrysanthemate, (b) 2.5–50% by weight of a fatty acid ester of 16–19 carbon atoms; (c) 2.5–30% by weight of a sorbitan fatty acid ester; (d) 0.5–1% by weight of at least one alcohol selected from the group consisting of ethanol, 1-propanol, 2-propanol, ethylene glycol, diethylene glycol, triethylene glycol, propylene glycol, dipropylene glycol, butylene glycol and glycerin; and (e) 40–93.5% by weight of a saturated hydrocarbon of 8–18 carbon atoms. This pre-mix insecticidal composition exhibits little, if any, precipitation when left to stand. It is sufficiently stable to be transported and is storage stable prior to formulating an insecticidal aerosol composition. A useful insecticidal aerosol composition contains 5–30% by weight of this pre-mix insecticidal composition, 40–85% by weight of water and 10–50% by weight of a propellant. The aerosol composition is stable, i.e. the separation into aqueous phase and organic phase occurs at a very low rate after shaking. A method for controlling harmful insects is also disclosed.

20 Claims, No Drawings

INSECTICIDAL AEROSOL COMPOSITION AND INSECTICIDAL COMPOSITION FOR PREPARATION OF SAME

BACKGROUND OF THE INVENTION

The present invention relates to an insecticidal aerosol composition and an insecticidal composition used for the preparation of the aerosol composition.

2,4-Dioxo-1-(2-propynyl)imidazolidin-3-ylmethyl chrysanthemate is an insecticidal compound disclosed in U.S. Pat. No. 4,176,189, and it is known in GB2,243,297B that the insecticidal activity of the compound, especially against cockroaches, is enhanced by the addition of some ester compounds.

However, there have been known no insecticidal water based aerosol compositions containing 2,4-dioxo-1-(2-propynyl)imidazolidin-3-ylmethyl chrysanthemate as an active ingredient which are enhanced in control effect against cockroaches and excellent in stability. Especially, in the case of water based aerosols, since they readily separate into an aqueous phase (emulsion) and an organic phase, even if they are shaken before spraying, separation into aqueous phase and organic phase occurs during spraying and as a result the insecticidal activity often becomes changeable.

SUMMARY OF THE INVENTION

The present invention provides an insecticidal aerosol composition which is a water based aerosol containing 2,4-dioxo-1-(2-propynyl)imidazolidin-3-ylmethyl chrysanthemate as an active ingredient and is excellent in stability i.e., the separation into aqueous phase and organic phase occurs at a very low rate after shaking it, and further provides an insecticidal composition used for preparing the aerosol composition.

The insecticidal composition of the present invention comprises (a) 0.1–10% by weight of 2,4-dioxo-1-(2-propynyl)imidazolidin-3-ylmethyl chrysanthemate, (b) 2.5–50% by weight of a fatty acid ester of 16–19 carbon atoms, (c) 2.5–30% by weight of a sorbitan fatty acid ester, (d) 0.5–1% by weight of at least one alcohol selected from the group consisting of ethanol, 1-propanol, 2-propanol, ethylene glycol, diethylene glycol, triethylene glycol, propylene glycol, dipropylene glycol, butylene glycol and glycerin, preferably propylene glycol, and (e) 40–93.5% by weight of a saturated hydrocarbon of 8–18, preferably a straight chain saturated hydrocarbon of 12–16 carbon atoms. This insecticidal composition is also excellent in the storage stability of the active ingredients.

The insecticidal aerosol composition of the present invention comprising 5–30% by weight of the above-mentioned insecticidal composition, 40–85% by weight of water and 10–50% by weight of a propellant is a water based aerosol which is excellent in stability i.e., the separation into aqueous phase and organic phase occurs at a very low rate after shaking. Moreover, the insecticidal aerosol composition of the present invention has sufficient knock-down efficiency and insecticidal activity, and active ingredient contained therein are stable during storage.

DESCRIPTION OF THE INVENTION

In the present invention, as the fatty acid esters of 16–19 carbon atoms, esters disclosed in GB2,243,297B are used, and from the point of stability of the insecticidal composition, monocarboxylic acid esters are preferred and examples thereof include isopropyl myristate, isopropyl palmitate, hexyl laurate and the like.

The sorbitan fatty acid esters used in the present invention are generally known as emulsifiers, and examples of the sorbitan fatty acid esters are sorbitan monolaurate, sorbitan monooleate and the like. Commercially available Rheodol SP-L10 (sorbitan monolaurate produced by Kao Co., Ltd.) and Rheodol SP-O10 (sorbitan monooleate produced by Kao Co., Ltd.) may be used.

Examples of saturated hydrocarbons of 8–18 carbon atoms used in the present invention include normal saturated hydrocarbon (normal-paraffinic hydrocarbon), branched saturated hydrocarbon (isoparaffinic hydrocarbon), cyclic saturated hydrocarbon (naphthenic hydrocarbon). Commercially available Norpar 15 (normal-paraffinic hydrocarbon of 14–18 carbon atoms produced by Exxon Chemical Co., Ltd.). Neo-chiozol (normal-paraffinic hydrocarbon of 12–14 carbon atoms produced by Chuo Kasei Kogyo Co., Ltd.), Exxsol D-40 (naphthenic hydrocarbon of 8–11 carbon atoms and paraffin produced by Exxon Chemical Co., Ltd.), Exxsol D-80 (naphthenic and paraffinic hydrocarbon of 10–13 carbon atoms produced by Exxon Chemical Co., Ltd.) and Isopar G (isoparaffinic hydrocarbon of 9–11 carbon atoms produced by Exxon Chemical Co., Ltd.) may be used.

In addition to the above ingredients (a)–(e), the insecticidal composition of the present invention may contain other insecticidal active ingredients, synergists, stabilizers and the like.

Examples of the other insecticidal active ingredients include phenothrin, cyphenothrin, permethrin, cypermethrin, deltamethrin, fenvalerate, esfenvalerate, ethofenprox, propoxur and the like. They are contained in an amount of about 0–15% by weight in the insecticidal composition of the present invention. Examples of the synergists include piperonyl butoxide, MGK264, N-(2-ethylhexyl)-1-isopropyl-4-methylbicyclo-[2.2.2]oct-5-en-2,3-dicarboximide, octachlorodipropyl ether and the like. The synergists are contained in an amount of about 0–20% by weight in the insecticidal composition of the present invention. Examples of the stabilizers include phenol derivatives such as BHT and BHA, bisphenol derivatives, arylamines such as phenyl-α-napthylamine, phenyl-β-naphthylamine and condensates of phenetidine and acetone; benzophenone compounds and the like.

The insecticidal aerosol composition of the present invention is obtained by introducing water and the insecticidal composition of the present invention into an aerosol container and charging propellant thereinto. If necessary, a metal corrosion inhibitor and a preservative such as sodium benzoate and ammonium benzoate, a perfume and the like may further be added to the insecticidal aerosol composition of the present invention.

The propellant includes liquefied petroleum gas, dimethyl ether, mixtures thereof and the like.

Water used is preferably deionized water or distilled water.

The insecticidal aerosol composition of the present invention is most suitable for control of cockroaches utilizing its knock-down activity of excellent rapid action and is used for control of cockroaches such as German cockroach (*Blattella germanica*), smokybrown cockroach (*Periplaneta fuliginosa*), American cockroach (*Periplaneta americana*), brown cockroach (*Periplaneta brunnea*), oriental cockroach (*Blatta orientalis*), lobster cockroach (*Nauphoeta cinerea*), Japanese cockroach (*Periplaneta japonica*), Australian cockroach (*Periplaneta australasiae*), brown-handed cockroach (*Supella longipalpa*), Madeira cockroach (*Leucophaea maderae*), and *Neostylopyga rhombifolia*. The composition is also effective for control of other harmful insects, for example, those of the Diptera, e.g., mosquitoes such as *Culex pipiens pallens, Culex tritaeniorhynchus, Aedes aegypti* and *Anopheles sinensis*; midges; house flies such as *Musca domestica, Muscina stabulans, Fannia canicularis*; flesh flies; arthomyiid flies; onion maggot; fruit flies; vinegar flies; moth flies; ghats; soldier flies; and so on; those of the Hymenoptera, e.g., ants; hornets; bethylid wasps; sawflies; and the like; those of the Isoptera, e.g., *Coptotermes formosanus* Shiraki; *Reticulitermes speratus*; and so on.

The insecticidal composition of the present invention is the so-called premix (industrial intermediate) used for preparation of the insecticidal aerosol composition of the present invention. The insecticidal composition hardly causes problem of precipitation while it is left to stand in room temperature. Therefore, the insecticidal composition is a suitable composition for transportation and storage for the preparation of the insecticidal aerosol composition of the present invention.

The present invention will be explained in more detail by the following examples.

First, preparation examples of the insecticidal composition of the present invention are shown.

EXAMPLE 1

1.6% by weight of 2,4-dioxo-1-(2-propynyl)-imidazolidin-3-ylmethyl 1R-cis,trans-chrysanthemate (hereinafter referred to as "imiprothrin"), 20% by weight of isopropyl myristate, 6% by weight of Rheodol SP-L10 (mentioned above), 0.5% by weight of propylene glycol and 71.9% by weight of Norpar 15 (mentioned above) were mixed to obtain an insecticidal composition (1) of the present invention.

The insecticidal composition (1) was left to stand at room temperature for one day and then observed to find no precipitation and it remained homogeneous.

EXAMPLE 2

An insecticidal composition (2) of the present invention was obtained in the same manner as in Example 1, except that 20% by weight of isopropyl palmitate was used in place of 20% by weight of isopropyl myristate.

The insecticidal composition (2) was left to stand at room temperature for one day and then observed to find no precipitation and it remained homogeneous.

EXAMPLE 3

2% by weight of imiprothrin, 22% by weight of isopropyl myristate, 10% by weight of Rheodol SP-L10 (mentioned above), 1% by weight of propylene glycol and 65% by weight of Neo-chiozol (mentioned above) were mixed to obtain an insecticidal composition (3) of the present invention.

EXAMPLE 4

3% by weight of imiprothrin, 20% by weight of isopropyl myristate, 10% by weight of Rheodol SP-L10 (mentioned above), 0.5% by weight of propylene glycol and 66.5% by weight of Neo-chiozol (mentioned above) were mixed to obtain an insecticidal composition (4) of the present invention.

EXAMPLE 5

An insecticidal composition (5) of the present invention was obtained in the same manner as in Example 4, except that isopropyl myristate was used in an amount of 40% by weight in place of 20% by weight and Neo-chiozol was used in an amount of 46.5% by weight in place of 66.5% by weight.

EXAMPLE 6

1.6% by weight of imiprothrin, 21.6% by weight of isopropyl myristate, 6% by weight of Rheodol SP-L10 (mentioned above), 0.5% by weight of propylene glycol and 70.3% by weight of Norpar 15 (mentioned above) were mixed to obtain an insecticidal composition (6) of the present invention.

EXAMPLE 7

1.6% by weight of imiprothrin, 4% by weight of MGK 264 (synergist), 21.6% by weight of isopropyl myristate, 6% by weight of Rheodol SP-L10 (mentioned above), 0.5% by weight of propylene glycol and 66.3% by weight of Norpar 15 (mentioned above) were mixed to obtain an insecticidal composition (7) of the present invention.

EXAMPLE 8

0.4% by weight of imiprothrin, 1.2% by weight of (S)-α-cyano-3-phenoxybenzyl 1R-trans-chrysanthemate (other insecticidal active ingredient), 20% by weight of isopropyl myristate, 6% by weight of Rheodol SP-L10 (mentioned above), 0.5% by weight of propylene glycol and 71.9% by weight of Norpar 15 (mentioned above) were mixed to obtain an insecticidal composition (8) of the present invention.

EXAMPLE 9

0.4% by weight of imiprothrin, 1.2% by weight of esfenvalerate (other insecticidal active ingredient), 20% by weight of isopropyl myristate, 6% by weight of Rheodol SP-L10 (mentioned above), 0.5% by weight of propylene glycol and 71.9% by weight of Norpar 15 (mentioned above) were mixed to obtain an insecticidal composition (9) of the present invention.

EXAMPLE 10

0.4% by weight of imiprothrin, 1.2% by weight of cypermethrin (other insecticidal active ingredient), 20% by weight of isopropyl myristate, 6% by weight of Rheodol SP-L10 (mentioned above), 0.5% by weight of propylene glycol and 71.9% by weight of Norpar 15 (mentioned above) were mixed to obtain an insecticidal composition (10) of the present invention.

EXAMPLE 11

1.6% by weight of imiprothrin, 10.0% by weight of MGK 264 (synergist), 11.6% by weight of isopropyl myristate, 6.0% by weight of Rheodol SP-L10 (mentioned above), 0.5% by weight of propylene glycol and 70.3% by weight of Norpar 15 (mentioned above) were mixed to give an insecticidal composition (11) of the present invention.

EXAMPLE 12

1.6% by weight of imiprothrin, 21.6% by weight of isopropyl myristate, 5.0% by weight of Rheodol SP-L10 (mentioned above), 0.5% by weight of propylene glycol and 71.3% by weight of Norpar 15 (mentioned above) were mixed to give an insecticidal composition (12) of the present invention.

EXAMPLE 13

0.5% by weight of imiprothrin, 0.5% by weight of (S)-α-cyano-3-phenoxybenzyl 1R-trans-chrysanthemate (other insecticidal active ingredient), 2.5% by weight of isopropyl myristate, 2.5% by weight of Rheodol SP-O10 (mentioned above), 0.5% by weight of propylene glycol and 93.5% by weight of Exxsol D-40 were mixed to give an insecticidal composition (13) of the present invention.

EXAMPLE 14

0.5% by weight of imiprothrin, 0.5% by weight of esfenvalerate (other insecticidal active ingredient), 2.5% by weight of isopropyl myristate, 2.5% by weight of Rheodol SP-O10 (mentioned above), 0.5% by weight of propylene glycol and 93.5% by weight of Exxsol D-40 (mentioned above) were mixed to give an insecticidal composition (14) of the present invention.

EXAMPLE 15

0.5% by weight of imiprothrin, 0.5% by weight of esfenvalerate (other insecticidal active ingredient), 2.5% by weight of isopropyl myristate, 2.5% by weight of Rheodol SP-O10 (mentioned above), 0.5% by weight of propylene glycol and 93.5% by weight of Exxsol D-80 (mentioned above) were mixed to give an insecticidal composition (15) of the present invention.

EXAMPLE 16

0.4% by weight of imiprothrin, 0.4% by weight of (S)-α-cyano-3-phenoxybenzyl 1R-trans-chrysanthemate (other insecticidal active ingredient), 20.4% by weight of isopropyl myristate, 5.0% by weight of Rheodol SP-L10 (mentioned above), 0.5% by weight of propylene glycol and 73.3% by weight of Neo-chiozol (mentioned above) were mixed to give an insecticidal composition (16) of the present invention.

EXAMPLE 17

0.4% by weight of imiprothrin, 0.4% by weight of esfenvalerate (other insecticidal active ingredient), 20.4% by weight of isopropyl myristate, 5.0% by weight of Rheodol SP-L10 (mentioned above), 0.5% by weight of propylene glycol and 73.3% by weight of Neo-chiozol (mentioned above) were mixed to give an insecticidal composition (17) of the present invention.

EXAMPLE 18

0.4% by weight of imiprothrin, 0.4% by weight of cypermethrin (other insecticidal active ingredient), 20.4% by weight of isopropyl myristate, 5.0% by weight of Rheodol SP-L10 (mentioned above), 0.5% by weight of propylene glycol and 73.3% by weight of Neo-chiozol (mentioned above) were mixed to give an insecticidal composition (18) of the present invention.

EXAMPLE 19

1.0% by weight of imiprothrin, 1.0% by weight of (S)-α-cyano-3-phenoxybenzyl 1R-trans-chrysanthemate (other insecticidal active ingredient), 6.0% by weight of isopropyl myristate, 12.5% by weight of Rheodol SP-L10 (mentioned above), 0.5% by weight of propylene glycol and 79.0% by weight of Neo-chiozol (mentioned above) were mixed to give an insecticidal composition (19) of the present invention.

EXAMPLE 20

1.5% by weight of imiprothrin, 0.5% by weight of (S)-α-cyano-3-phenoxybenzyl 1R-trans-chrysanthemate (other insecticidal active ingredient), 5.5% by weight of isopropyl myristate, 5.0% by weight of Rheodol SP-L10 (mentioned above), 0.5% by weight of propylene glycol and 87.0% by weight of Isopar G (mentioned above) were mixed to give an insecticidal composition (20) of the present invention.

Examples of stability test on the insecticidal aerosol compositions obtained from the insecticidal composition of the present invention are shown below.

EXAMPLE 21

A glass aerosol which the state of liquid contained therein can be observed was made using 20 parts by weight of the insecticidal composition, 50 parts by weight of deionized water and 30 parts by weight of liquefied petroleum gas. After storing for 1 week at 25° C., the glass aerosol was repeatedly erected and inverted 20 times at an interval of 2 seconds. Thereafter, it was erected on a horizontal stand and the rate of separation of the mixture in the glass container into an aqueous phase and an organic phase was measured. The rate of the separation was expressed by the time required for the width of the separated organic phase becoming 20% of the whole width. The results are shown in Table 1.

Comparative Example 1 in Table 1 shows the result in the case of using an insecticidal composition obtained in the same manner as in Example 3, except that propylene glycol in an amount of 1% by weight was not used and instead, additional 1% by weight of Neo-chiozol was used, and Comparative Example 2 shows the result in the case of using an insecticidal composition obtained in the same manner as in Example 3, except that isopropyl myristate in an amount of 22% by weight was not used and instead, additional 22% by weight of Neo-chiozol was used.

TABLE 1

|  | Time required for the separated organic phase becoming 20% (second) |
|---|---|
| Insecticidal composition (3) | 51 |
| Comparative Example 1 | 20 |
| Comparative Example 2 | 20 |

As can be seen from the above table, the insecticidal aerosol composition of the present invention can keep a stable emulsion of the insecticidal composition, water and propellant over a long period of time.

EXAMPLE 22

25% by weight of the insecticidal composition of the present invention and 55% by weight of 0.2% by weight of an aqueous ammonium benzoate solution were charged in an aerosol container. After the container was fitted with an aerosol valve, 20% by weight of liquefied petroleum gas was charged through the valve portion to prepare an aerosol composition. The test aerosol composition was stored at 40° C. for 6 months. The content of the ingredients was analyzed with gas chromatography to obtain the residual rate. Table 2 shows the result.

TABLE 2

|  | Residual Rate (%) | |
| --- | --- | --- |
|  | Imiprothrin | MGK 264 |
| Insecticidal composition (7) | 100 | 100 |
| Insecticidal composition (12) | 100 | — |

EXAMPLE 23

20% by weight of the insecticidal composition of the present invention and 60% by weight of deionized water were charged in an aerosol container. After the container was fitted with a valve, 20% by weight of liquefied petroleum gas was charged through the valve portion to obtain an aerosol composition. The test aerosol composition was stored at 40° C. for 3 months. The content of the active ingredient was analyzed with a gas chromatography to obtain the residual rate. Table 3 shows the result.

TABLE 3

|  | Residual Rate (%) | |
| --- | --- | --- |
|  | Imiprothrin | Other active ingredient |
| Insecticidal composition (13) | 100 | 95.1 |
| Insecticidal composition (14) | 100 | 93.5 |

Insecticidal test examples on the insecticidal aerosol compositions of the present invention are shown below.

EXAMPLE 24

Ten (five males and five females) German cockroaches (*Blattella germanica*) were released in a cylindrical vessel (diameter: 13 cm, height: 10 cm) having a net of 40 mesh wire at 1 cm from the bottom. The vessel was put into a glass cylinder (diameter: 20 cm, height: 60 cm). Then, a predetermined amount of an aerosol to be tested was sprayed onto the cockroaches and the glass cylinder was quickly covered up. Thirty seconds after spraying, the vessel was taken out from the glass cylinder. The number of the knocked down cockroaches was counted at 1, 2, 3, 5, 7, 10, 15 and 20 minutes after spraying.

The test was replicated 5 times and from the average of the results, $KT_{50}$ value (time required for 50% of cockroaches being knock-down) was obtained by calculation by Blis' probit method. The results are shown in Table 4.

TABLE 4

| Ingredients of given aerosol composition and the composition (% by weight) | Sprayed amount (g) | $KT_{50}$ value (min) |
| --- | --- | --- |
| Insecticidal composition(4): 10<br>Deionized water: 50<br>Liquefied petroleum gas: 40 | 0.3 | 2.3 |
| Insecticidal composition(5): 10<br>Deionized water: 50<br>Liquefied petroleum gas: 40 | 0.3 | 3.1 |
| Insecticidal composition(6): 25<br>0.2 wt % ammonium benzoate solution: 55<br>Liquefied petroleum gas: 20 | 0.3 | 0.9 |
| Insecticidal composition(7): 25<br>0.2 wt % ammonium benzoate solution: 55<br>Liquefied petroleum gas: 20 | 0.6 | 0.7 |
| Insecticidal composition(11): 25<br>0.2 wt % ammonium benzoate solution: 55<br>Liquefied petroleum gas: 20 | 0.4 | $\leq 0.7$ |
| Insecticidal composition(12): 25<br>0.2 wt % ammonium benzoate solution: 55<br>Liquefied petroleum gas: 20 | 0.6 | $\leq 0.7$ |

EXAMPLE 25

25% by weight of the insecticidal composition of the present invention and 55% by weight of 0.2 wt.% ammonium benzoate solution were introduced in an aerosol container. After the container was fitted with a valve, 20% by weight of liquefied petroleum gas was charged under pressure through the valve portion to prepare an aerosol composition. 1.0 g of the aerosol composition was uniformly sprayed perpendicularly from a height of 20 cm on a decorative laminate sheet of 15 cm×15 cm. Cylindrical plastics of 18 cm in diameter and 5 cm in height in which margarine had been applied on the inner surface for preventing cockroaches from escaping were put on each sheet. Ten (five female and five male) German cockroaches (*Blattella germanica*: resistant strain to pyrethroids) were released in the cylindrical plastic and they were compulsorily contacted to the test composition under test for 2 hours. Thereafter the number of the knock-down cockroaches was counted. The test was replicated 3 times and the $KT_{50}$ value (time required for 50% of the cockroaches being knocked down) was obtained from the knock-down ratio against the elapsed time according to Finney's diagrammatic method. Further cockroaches under test were moved into a cup containing water and bait and after 3 days, the mortality thereof was observed. A series of the tests were replicated using the same decorative laminate sheet after 1, 5, 14, 21 and 28 days of the aerosol spraying treatment. In the interval of the test the decorative laminate sheets were stored at 25° C. The results were shown in Tables 5 and 6.

TABLE 5

|  | $KT_{50}$ (min) | | | | |
| --- | --- | --- | --- | --- | --- |
|  | after 1 day | 5 days | 14 days | 21 days | 28 days |
| Insecticidal composition (16) | <2.5 | <2.5 | <2.5 | <2.5 | <2.5 |
| Insecticidal composition (17) | <2.5 | <2.5 | <2.5 | <2.5 | 3.5 |
| Insecticidal composition (18) | <2.5 | <2.5 | <2.5 | <2.5 | 5.6 |

TABLE 6

| | Mortality (%) | | | | |
|---|---|---|---|---|---|
| | after 1 day | 5 days | 14 days | 21 days | 28 days |
| Insecticidal composition (16) | 100 | 100 | 100 | 100 | 100 |
| Insecticidal composition (17) | 100 | 100 | 100 | 100 | 100 |
| Insecticidal composition (18) | 100 | 100 | 100 | 100 | 97 |

The insecticidal aerosol composition of the present invention has a suitable property for water based aerosol, i.e. the separation into aqueous phase and organic phase occurs at very low rate, so that it shows the constant excellent insecticidal effect. Moreover, the insecticidal composition of the present invention which is a premix for the aerosol composition is stable with substantially no problems of precipitation when left to stand and is a suitable starting composition in transportation and storage for preparation of the insecticidal aerosol composition of the present invention.

What is claimed is:

1. An insecticidal composition which comprises (a) 0.1–10% by weight of 2,4-dioxo-1-(2-propynyl)-imidazolidin-3-ylmethyl chrysanthemate, (b) 2.5–50% by weight of a fatty acid ester of 16–19 carbon atoms, (c) 2.5–30% by weight of a sorbitan fatty acid ester, (d) 0.5–1% by weight of at least one alcohol selected from the group consisting of ethanol, 1-propanol, 2-propanol, ethylene glycol, diethylene glycol, triethylene glycol, propylene glycol, dipropylene glycol, butylene glycol and glycerin and (e) 40–93.5% by weight of a saturated hydrocarbon of 8–18 carbon atoms.

2. An insecticidal composition according to claim 1 wherein the component (d) is propylene glycol.

3. An insecticidal composition according to claim 1, wherein said fatty acid ester of 16–19 carbon atoms is a monocarboxcylic acid ester.

4. An insecticidal composition according to claim 1, wherein said fatty acid ester of 16–19 carbon atoms is at least one of isopropyl myristate, isopropyl palmitate or hexyl laurate.

5. An insecticidal composition according to claim 1, wherein said saturated hydrocarbon of 8–18 carbon atoms comprises a normal-paraffinic hydrocarbon having 14–18 carbon atoms, a normal-paraffinic hydrocarbon having 12–14 carbon atoms, a naphthenic hydrocarbon having 8–11 carbon atoms, an isoparaffinic hydrocarbon having 9–11 carbon atoms, or a naphthenic and paraffinic hydrocarbon having 10–13 carbon atoms.

6. An insecticidal composition according to claim 2, wherein said fatty acid ester of 16–19 carbon atoms is at least one of isopropyl myristate, isopropyl palmitate or hexyl laurate.

7. A method for preparing a storage-stable and transportable insecticidal premix composition which comprises mixing (a) 0.1–10% by weight of 2,4-dioxo-1-(2-propynyl)-imidazolidin-3-ylmethyl chrysanthemate, (b) 2.5–50% by weight of a fatty acid ester of 16–19 carbon atoms, (c) 2.5–30% by weight of a sorbitan fatty acid ester, (d) 0.5–1% by weight of at least one alcohol selected from the group consisting of ethanol, 1-propanol, 2-propanol, ethylene clycol, diethylene glycol, triethylene glycol, propylene glycol, dipropylene glycol, butylene glycol and glycerin and (e) 40–93.5% by weight of a saturated hydrocarbon of 8–18 carbon atoms, whereby said storage stable and transportable insecticidal premix composition is obtained.

8. A method according to claim 7, wherein the component (d) comprises propylene glycol.

9. A method according to claim 7, wherein said fatty acid ester of 16–19 carbon atoms is a monocarboxcylic acid ester.

10. A method according to claim 7, wherein said fatty acid ester of 16–19 carbon atoms is at least one of isopropyl myristate, isopropyl palmitate or hexyl laurate.

11. A method according to claim 7, wherein said saturated hydrocarbon of 8–18 carbon atoms comprises a normal-paraffinic hydrocarbon having 14–18 carbon atoms, a normal-paraffinic hydrocarbon having 12–14 carbon atoms, a naphthenic hydrocarbon having 8–11 carbon atoms, an isoparaffinic hydrocarbon having 9–11 carbon atoms, or a naphthenic and paraffinic hydrocarbon having 10–13 carbon atoms.

12. An insecticidal aerosol composition formulated from constituents which comprise:

5–30% by weight of an insecticidal premix composition comprising (a) 0.1–10% by weight of 2,4-dioxo-1-(2-propynyl)-imidazolidin-3-ylmethyl chrysanthemate, (b) 2.5–50% by weight of a fatty acid ester of 16–19 carbon atoms, (c) 2.5–30% by weight of a sorbitan fatty acid ester, (d) 0.5–1% by weight of at least one alcohol selected from the group consisting of ethanol, 1-propanol, 2-propanol, ethylene clycol, diethylene glycol, triethylene glycol, propylene glycol, dipropylene glycol, butylene glycol and glycerin and (e) 40–93.5% by weight of a saturated hydrocarbon of 8–18 carbon atoms;

40–85% by weight of water; and

10–50% by weight of a propellant.

13. An insecticidal aerosol composition according to claim 12, wherein said insecticidal premix composition, the component (d) comprises propylene glycol.

14. An insecticidal composition according to claim 12, wherein said fatty acid ester of 16–19 carbon atoms is a monocarboxcylic acid ester.

15. An insecticidal composition according to claim 12, wherein said fatty acid ester of 16–19 carbon atoms is at least one of isopropyl myristate, isopropyl palmitate or hexyl laurate.

16. An insecticidal composition according to claim 12, wherein said saturated hydrocarbon of 8–18 carbon atoms comprises a normal-paraffinic hydrocarbon having 14–18 carbon atoms, a normal-paraffinic hydrocarbon having 12–14 carbon atoms, a naphthenic hydrocarbon having 8–11 carbon atoms, an isoparaffinic hydrocarbon having 9–11 carbon atoms, or a naphthenic and paraffinic hydrocarbon having 10–13 carbon atoms.

17. A method for controlling harmful insects comprising applying the insecticidal aerosol composition according to claim 12 to said insects.

18. A method for controlling cockroaches comprising applying the insecticidal aerosol composition according to claim 12 to said cockroaches.

19. A method for controlling harmful insects which comprises applying the insecticidal aerosol composition according to claim 13 to said harmful insects.

20. A method for controlling cockroaches which comprises applying the insecticidal aerosol composition according to claim 13 to said cockroaches.

* * * * *